United States Patent [19]

Dragan

[11] Patent Number: 4,682,950
[45] Date of Patent: Jul. 28, 1987

[54] DEVICE AND METHOD OF BONDING AND VENEERING DENTAL MATERIAL TO A TOOTH

[76] Inventor: William B. Dragan, 85 Burr St., Easton, Conn. 06612

[21] Appl. No.: 792,803

[22] Filed: Oct. 30, 1985

[51] Int. Cl.⁴ .............................................. A61C 5/04
[52] U.S. Cl. ................................... 433/90; 433/215; 222/575; 264/19
[58] Field of Search .................... 433/90, 89, 215; 222/575, 326, 146.5; 264/16, 19, 20

[56] References Cited

U.S. PATENT DOCUMENTS

| | | | |
|---|---|---|---|
| 559,120 | 4/1896 | Clark | 222/575 |
| 878,182 | 2/1908 | Blake | 222/575 |
| 2,648,906 | 8/1953 | Holmes | 433/90 |
| 3,858,985 | 1/1975 | Fiveash | 222/146.5 |
| 3,943,628 | 3/1976 | Kronman et al. | 433/89 |
| 4,391,590 | 7/1983 | Dougherty | 433/90 |

Primary Examiner—John J. Wilson
Attorney, Agent, or Firm—Arthur T. Fattibene

[57] ABSTRACT

An applicating device and method of cosmetic bonding and veneering of teeth with composite dental material which includes a disposable syringe tip defining a reservoir for containing a predetermined amount of composite dental material and having connected thereto a discharge end portion which narrows to a rectangularly shaped discharge orifice having a width of approximately 0.5 mm and a length of approximately 4 to 6 mm. A piston or plug seals the end of the reservoir portion and which piston is displaceably disposed in the reservoir portion. The discharge orifice is provided with a sealing cap when not in use. The method of bonding and veneering a dental material on a tooth includes the step of expressing a flat thin ribbon veneer of composite material directly onto the tooth. The composite material is formed in a thin uniform flat strip of not more than 0.5 mm in thickness and approximately 4 to 6 mm. in width by expressing it through the discharge opening of a syringe tip. Depending upon the nature of the composite material, the tip may be of varying degrees of opacity from clear to black.

10 Claims, 8 Drawing Figures

DEVICE AND METHOD OF BONDING AND VENEERING DENTAL MATERIAL TO A TOOTH

FIELD OF INVENTION

This invention related to a dental applicating device in the form of a disposable tip adapted to be used with a syringe device of the kind disclosed in any of my prior U.S. patents, viz. U.S. Pat. Nos. 3,581,399; 3,900,954; or 4,198,756, and a technique of veneering teeth for cosmetic purposes or the like.

PROBLEM AND PRIOR ART

My prior above identified patents relate to dental syringes and disposable tips for use therewith for the placement of composite dental filling material in a tooth cavity for restoring decayed teeth. Others have adopted the syringe technique as disclosed in my foregoing patents for applying composite resin material to a cavity of a tooth as evidenced by U.S. Pat. Nos. 4,295,828; 4,330,280; 4,384,853 and 4,391,590. However, the disposable tips disclosed in the foregoing identified patents are not particularly suitable to procedures relating to the bonding and/or veneering teeth with composite dental material for cosmetic purposes.

Heretofore, dentists bonded and/or veneered teeth for various cosmetic reasons in any one of several primative ways. One technique was to take a bulk amount of the composite material and form it into a pancake by fingering the material and then placing the so-formed pancake onto the tooth and thereafter forming the same as may be required. Another technique was to place a bulk supply of the composite material on a tooth with a spatula and thereafter forming the same by spreading the material with the spatula. Another technique was to take an impression of the teeth which was sent to a dental laboratory where the dental technician would fabricate the veneer on the model using one of the foregoing described methods.

In the cosmetic bonding or veneering of teeth, it is important to keep the veneer material as thin as possible. This is because very little tooth reduction (0.5 mm or less) or no tooth reduction is done on the labial or lip portion of the tooth to be veneered. It is important to keep the veneer as thin as possible for the further reason that the patient is very conscious of even the slightest change in the thickness of a tooth, e.g. a front tooth. Therefore, in doing a cosmetic veneer or bonding, it is imperative to keep the veneer as thin as possible, and ideally not more than 0.5 mm thick.

Another problem encountered with the prior described techniques of bonding or veneering was that of foreign contamination, i.e., the handling of the cosmetic material by fingers or instruments in forming the bulk dental material to the desired thinness. Such contamination of the material defeats the cosmetic purpose of the procedure. The handling of the composite material by fingers or with instruments further tends to increase the formation of air voids and/or porosity in the veneer which will pick up and hold stains, thus rendering the veneer to discoloration and become unsightly, thus defeating the purpose and intent of the cosmetic procedure. Also, the use of fingers and/or instruments to form and shape the bulk material leaves much to the artistic ability of the practitioner. Also, the known techniques described herein result in much waste of unused exposed material, since much of the currently used material for performing a cosmetic procedure is light activated.

OBJECTS

An object of this invention is to provide a new technique for bonding and/or veneering teeth for cosmetic purposes by syringing the veneer material directly to a tooth in a very thin flat ribbon form.

Another object is to provide a disposable syringe tip which is formed so as to allow the material to be extruded therefrom in a very thin, flat, continuous ribbon.

SUMMARY OF THE INVENTION

The foregoing objects are obtained by syringing the composite material directly to the tooth to be veneered in thin, flat ribbons by utilizing a disposable syringe tip having a discharge orifice which is rectangular in shape, e.g. a discharge orifice having a width of approximately 0.5 mm and a length of 4 to 6mm. The tip is sized to fit a known dental syringe, and the tip may be either loaded with the appropriate material by the dentist or may be pre-loaded with the material by the manufacturer thereof.

FEATURES

A feature of this invention resides in a specifically formed dental nozzle tip having an elongated discharge opening which permits the dental cosmetic material therein to be extruded in a relatively thin flat ribbon form that can be applied directly to the tooth.

Another feature resides in the provision whereby the syringing of the cosmetic material in thin, flat ribbons directly to the tooth minimizes voids and resulting discoloration of the veneer.

Another feature resides in the provision wherein the application of the cosmetic material to the tooth in thin veneer strips enables a practitioner to more easily reproduce the anatomy of a tooth.

Another feature resides in a technique or method of applying cosmetic dental material to a tooth in a manner whereby the material can be readily shaped to the tooth structure with a minimum of waste and in a minimum of time.

Other features and advantages will become more readily apparent when considered in view of the drawings and specification in which.

DETAILED DESCRIPTION

Figure 1:
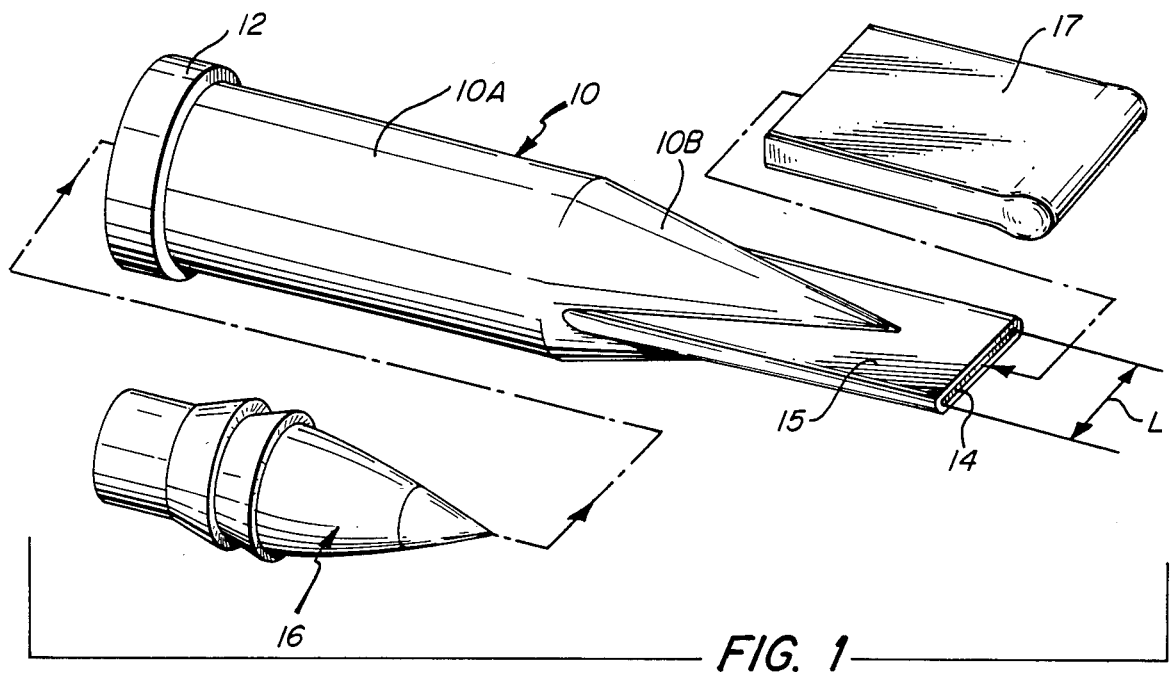
FIG. 1 is an exploded view of a disposable syringe tip embodying the invention.
Figure 2:
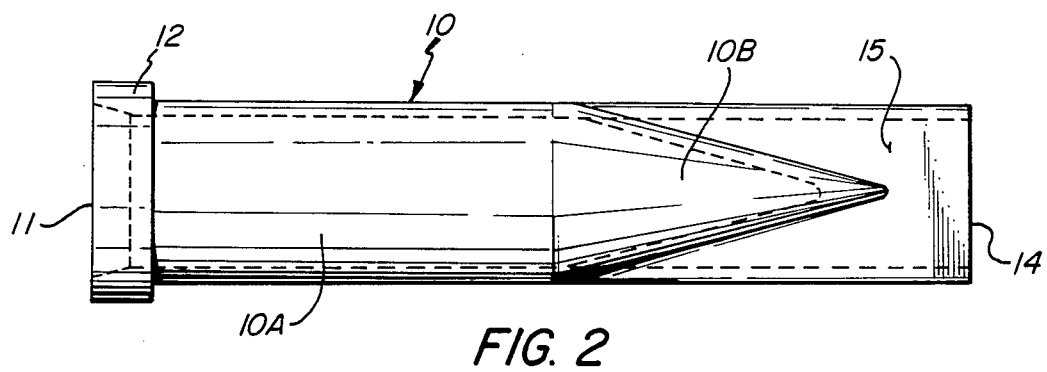
FIG. 2 is a top plan view of the disposable tip.
Figure 3:
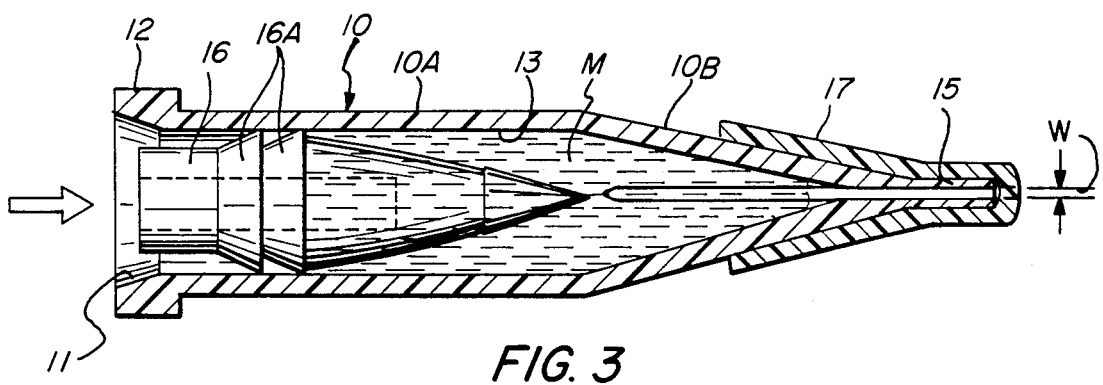
FIG. 3 is a sectional view of the tip.
Figure 4:
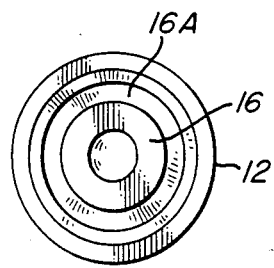
FIG. 4 is a rear view of FIG. 3.
Figure 5:
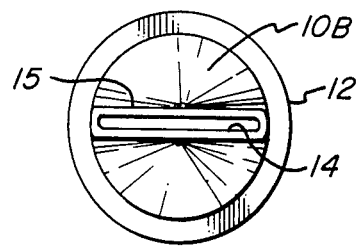
FIG. 5 is a front view of the tip of FIG. 2.

Referring to the drawings, there is illustrated a disposable syringe tip 10 which is particularly adapted for performing an improved method or technique for bonding and/or veneering a tooth with a composite resin material.

As shown in FIG. 1, the nozzle tip by which the bonding or veneering technique, as will be described herein, comprises a small tube or tip 10 having a body portion 10A of generally cylindrical shape. The rear end of the body portion 10A is provided with a full open end as indicated at 11. Circumscribing the full open end 11 is a flange 12 extending laterally outwardly. The body portion 10A defines a chamber or reservoir 13 for receiving a predetermined amount of a cosmetic composite resin material, bonding agent, or other material M, which the dentist may wish to apply to a tooth or an impression of a tooth, in thin, brushlike strokes for veneering or the like. As shown, the front portion 10B of the tip 10 tapers toward the discharge orifice or opening 14. As shown, the tapered front end portion 10B merges into a broad flattened nozzle or tip end 15 which defines the discharge orifice 14. As shown, the discharge orifice 14 defines an opening approximately 0.5 mm in thickness or width "W" and a length "L" of approximately 4 to 6 mm. The opening or orifice 14 is sized so that the material M extruded therefrom defines a thin, flat ribbon R of approximately the size of the orifice 14. The rear end of the body portion 10A is closed by a freely displaceable piston 16. As shown, the piston is provided with one or more wipers 16A disposed in sealing relationship to the internal walls of the body portion 10A. The piston 16 is also provided with a conical tip end complementing the internal shape of the tapering front end 10B. Thus, when the piston is displaced to extrude the material M, the complementary shape of the piston 16 and front end 10B of the tip 10 will insure that virtually all of the material M has been extruded therefrom when the piston has reached the end of its travel.

With the construction described, the tip 10 can be either loaded with material by the dentist, which may be of his own choosing or brand, or the tip can be loaded by the manufacturer of the material, and sold to the dentist as a loaded, pre-filled tube or tip which the dentist need only to place in his syringe. If desired, an end cap 17 may be fitted over the discharge end 15 of the tip to seal the front opening 14.

It will be understood that the tube or tip 10 may be pigmented to any suitable color and/or degree of opaqueness depending upon the nature and/or color or shade of the material M placed therein. For light activated composite material, the tip may be rendered light opaque. It will be understood that any colored or pigmented tube or tip may be used with light activated materials, providing that the tube or tip is protected from direct light.

Figure 6:
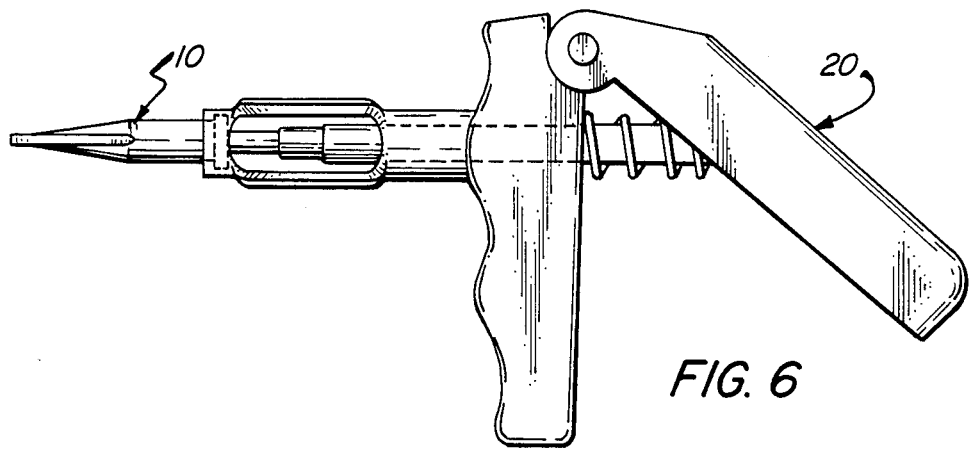
FIG. 6 is a side view of a syringe construction for use with the tip of FIG. 1.

FIG. 6 illustrates one of several syringe constructions 20 for use with the tip construction 10, as shown. The syringe construction illustrated is of the type disclosed in my U.S. Pat. No. 4,198,756. However, it will be understood that the tip 10 may be used with any of the prior known syringes as identified in the foregoing noted patents.

The method of bonding or veneering of teeth comprises first preparing a tooth structure to be veneered. This may be done by reducing the facial surface of the tooth to be cosmetically treated or veneered by approximately 0.5 mm, where necessary. In some instances, it may not be necessary to reduce the facial enamel. However, to insure that the veneered tooth does not look bulky or feel bulky to the lip, the tooth reduction step herein set forth is suggested and recommended. This procedure or step can normally be done without local anesthetic as the reduction of such a small amount of enamel is normally painless. Once the slight enamel reduction is completed, the tooth surface is polished with a watery slurry of pumice. The tooth is thereafter thoroughly washed off and dried. A mild (3.7%) phosphoric acid is then applied to the dry tooth for approximately one (1) minute. The tooth is then washed for at least 15 to 30 seconds. The tooth is again dried until a white chalky appearance becomes apparent. The white chalky appearance indicates a good etch as the result of the phosphoric acid step. The phosphoric acid step results in the creation of tiny microscopic undercuts and/or indentations which become the mechanical retention means for the composite veneer material. A thin liquid bonding material is then applied to the tooth which sinks or soaks into the microscopic undercuts and it functions as the gluing or adhering agent or mechanism for the composite resin to the tooth, after the thin layer of liquid bond is readied for receiving the composite resin veneer.

Figure 7:
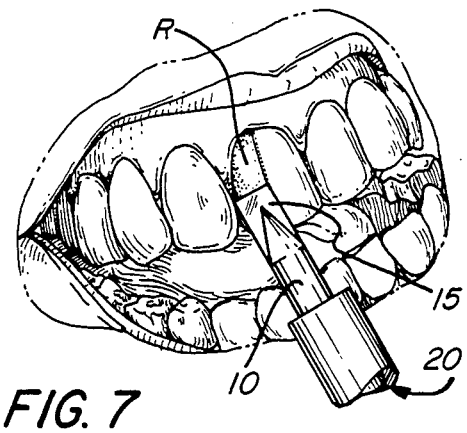
FIG. 7 illustrates the step of applying a veneer strip to a tooth.
Figure 8:
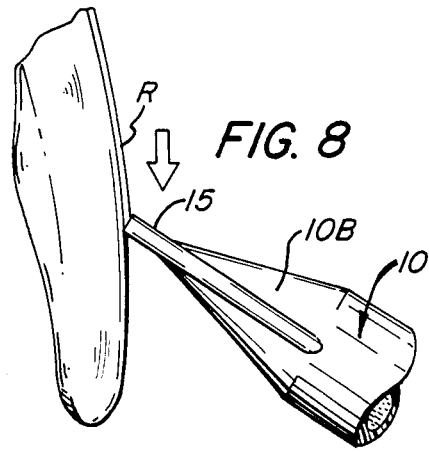
FIG. 8 is a side view of the veneer strip being applied to a tooth.

In accordance with this invention, the veneering step may be accomplished either directly or indirectly. The direct application of the veneer material may be accomplished by syringing the composite material directly onto the prepared tooth in thin, flat strips of ribbon material R which is formed by extruding the material from the syringe tip 10 herein described. Reference is made to FIGS. 7 and 8 wherein the resin material M is applied in thin strips R to the tooth. The strip so formed, i.e., approximately 0.5 mm thick and 4 to 6 mm. wide, is applied directly to the tooth. The material M is applied by starting at the gum line (gingival) and working toward the insical edge (biting edge). Usually, the front teeth can be veneered by applying two contiguous strips, one for each half of the tooth. For broad teeth, additional strips of veneer material may be applied. After the contiguous veneer strips have been applied to the tooth, the dentist need only to blend the contiguous edges of the adjacent strip by using any of the standard dental forming instruments. With the composite material now properly formed to the tooth, the composite resin is cured. With light activated material, this is effected by directing a light beam thereon. With chemically cured compositions, the material will automatically cure after a lapse of a predetermined time.

It will be apparent that the number of strips necessary to cover a tooth will vary depending upon the width of the tooth and the space to be veneered.

The same ribbon extruding step described herein can be utilized by a dental technician in forming a veneer on a plastic model of a particular person's tooth. In this technique, the dentist prepares the tooth and then makes a plaster mold of the prepared tooth. The mold or model is then sent to the lab where a technician applies the veneer material to the mold in the same manner as described above relative to the direct application.

The veneer so formed on the mold is permitted to set or cure as herein described and thereafter removed from the model and sent to the dentist to be installed directly on the patient's tooth. This is attained by applying the appropriate adhesive either to the back of the veneer or to the tooth, and press fitting the pre-formed veneer directly to the prepared tooth.

It will be understood that the described tip and technique of veneering can be utilized with either chemically activated composite material or light activated material. The technique described herein greatly facilitates the forming of the veneer and insures a veneer having a generally uniform thickness, and a minimum of voids. Also, the technique reduces the probability of contamination since the dentist need not finger or manually form the veneer. Also, the veneer of optimum or desired thickness can be formed with a minimum amount of material. The technique and tip described also minimizes the amount of artistic skill required by the dentist to form a satisfactory veneer, and at the same time allows the veneer to be formed and placed in a minimum of time.

The nozzle or tip 10 described herein is preferably formed of a suitable plastic material, thereby rendering the tip readily disposable. The shade of the veneering composite resin in the tip or nozzle can be readily ascertained by color coding either the nozzle tip 10 and/or the sealing cap 17 to the color of the contained material M. In the illustrated embodiment, the longitudinal axis of the orifice opening 14 is disposed co-plannar relative to a medial plane of the nozzle 10.

While the invention has been described with respect to a particular embodiment thereof, it will be understood and appreciated that variations and modifications may be made without departing from the spirit or scope of the invention.

What is claimed is:

1. A disposable dental syringe tip for packaging, dispensing and applying a dental tooth veneering material directly to a tooth comprising
   a plastic disposable nozzle having a generally cylindrical body portion defining a reservoir adapted to receive a predetermined amount of dental veneering material;
   a discharging tip portion terminating in a discharge orifice,
   said body portion having a full open end opposite said discharge orifice,
   a laterally extending external flange circumscribing said full open end,
   said cylindrical body portion converging toward said discharge orifice to define a conically shaped intermediate portion disposed between said cylindrical body portion and said discharge orifice, said conically shaped intermediate portion being axially disposed relative to said cylindrical body portion,
   said discharging tip portion defining a generally flat and broad rectangularly shaped discharge orifice.
   a piston disposed in said body portion for sealing said full open end,
   said piston being displaceably disposed in said body portion,
   said piston having a wiper portion for engaging the interior surface of said cylindrical body portion, and
   said piston having a conically shaped tip end adapted to compliment the intermediate conically shaped portion of said nozzle tip.
   said piston being slidably disposed within said body portion for ejecting the dental material therefrom when displaced, whereby substantially all of the material disposed in said nozzle tip can be expressed therefrom when said piston has been fully displaced within said cylindrical body portion.

2. A disposable dental syringe tip as defined in claim 1 and including a syringe having a plunger,
   said syringe tip being detachably connected to the end of said syringe,
   and said plunger being adapted to engage said piston to effect the displacement of said piston within said cylindrical body portion whereby the displacement of said piston causes the dental material to be extruded in a thin flat ribbon shape from said discharge orifice directly onto a tooth.

3. A dental material dispensing device as defined in claim 1, wherein said rectangular shape orifice is approximately 0.5 mm in width and having a length in the range of 8 to 12 times the width.

4. A dental material dispensing device as defined in claim 1, wherein the said discharge orifice is disposed co-planner relative to the longitudinal axis of said nozzle.

5. A disposable dental nozzle tip as defined in claim 1 and including a predetermined amount of dental veneering material disposed in said resevoir, and a readily detachable flattened sealing cap frictionally fitted to said flattened, broad discharging tip portion for sealing said discharge orifice when said syringe tip is not in use.

6. A method of veneering teeth comprising the steps of
   preparing a tooth structure for receiving a thin covering veneer of a composite resin material,
   and applying the thin covering veneer material in relatively thin flat ribbon strips to the prepared surface ot the tooth,
   said application of said covering veneer material being by syringing said material directly onto the tooth in said thin, flat ribbon shape whereby the forming of air void is minimized.

7. A method as defined in claim 6, wherein
   the covering veneer material is applied in one or more contiguously disposed flat thin ribbon shapes, and
   shaping said contiguously disposed thin flat ribbon shapes to blend the junction disposed between adjacent edges of said contiguous flat strips.

8. A method as defined in claim 6, and
   including the step of using a light activated composite resin as said veneer material, and
   curing said veneer material upon completion of the forming of said veneer material to the shape of the tooth by directing a light beam thereon.

9. A method of veneering a tooth with a cosmetic composite material comprising the steps of
   removing not more than 0.5 mm of the tooth enamel from the tooth to be veneered,
   polishing the tooth surface upon the removal of the surface enamel with a slurry of pumice,
   washing the tooth to effect removal of the pumice slurry and thereafter drying the tooth,
   etching the dried tooth by the application of a mild solution of phosphoric acid for approximately one (1) minute,
   cleansing the tooth by washing to remove any traces of the phosphoric acid,
   drying the cleansed tooth until a chalky appearance becomes apparent,
   coating the dry cleansed tooth with a bonding agent,
   and applying the cosmetic composite material to the tooth by syringing the material in thin, flat ribbon form one or more times to cover the surface to be veneered,
   blending the contiguous edges of said thin flat ribbon material,
   and curing the veneer material.

10. A method of indirectly forming a veneer on a tooth comprising the steps of
    preparing a tooth for receiving a veneer surface,
    taking a plastic mold of the prepared tooth, applying a thin flat ribbon strip of material by syringing a cosmetic composite material onto the plastic mold of the tooth to be veneered, forming the edges of the thin ribbon strip to conform to the tooth, curing the material shaped to the plastic mold tooth, removing the cured veneer material from the plastic mold, and adhering the removed veneer shape directly to the tooth to be veneered.

* * * * *